US012769603B2

(12) United States Patent
Chen et al.

(10) Patent No.: US 12,769,603 B2
(45) Date of Patent: Oct. 20, 2026

(54) METRIC AND LOG JOINT AUTOENCODER FOR ANOMALY DETECTION IN HEALTHCARE DECISION MAKING

(71) Applicant: NEC Laboratories America, Inc., Princeton, NJ (US)

(72) Inventors: Yuncong Chen, Jersey City, NJ (US); Haifeng Chen, West Windsor, NJ (US); LuAn Tang, Cranbury, NJ (US); Zhengzhang Chen, Princeton Junction, NJ (US)

(73) Assignee: NEC Corporation (JP)

( * ) Notice: Subject to any disclaimer, the term of this patent is extended or adjusted under 35 U.S.C. 154(b) by 64 days.

(21) Appl. No.: 18/599,322

(22) Filed: Mar. 8, 2024

(65) Prior Publication Data

US 2024/0303149 A1 Sep. 12, 2024

Related U.S. Application Data

(60) Provisional application No. 63/533,418, filed on Aug. 18, 2023, provisional application No. 63/450,986, filed on Mar. 9, 2023.

(51) Int. Cl.
*G16H 50/30* (2018.01)
*G06F 11/07* (2006.01)

(52) U.S. Cl.
CPC ........ *G06F 11/079* (2013.01); *G06F 11/0721* (2013.01); *G16H 50/30* (2018.01)

(58) Field of Classification Search
None
See application file for complete search history.

(56) References Cited

U.S. PATENT DOCUMENTS

| | | | | |
|---|---|---|---|---|
| 11,545,255 | B2 * | 1/2023 | Sun | G06V 10/82 |
| 2021/0349897 | A1 * | 11/2021 | Pierri | G06F 11/079 |
| 2023/0094355 | A1 * | 3/2023 | Filho | G06N 3/045 706/12 |
| 2023/0186053 | A1 * | 6/2023 | Andoni | G06N 3/045 706/21 |

OTHER PUBLICATIONS

Shvetsova et al. ("Anomaly Detection in Medical Imaging With Deep Perceptual Autoencoders," in IEEE Access, vol. 9, pp. 118571-118583, 2021) (Year: 2021).*

(Continued)

*Primary Examiner* — Christopher B Tokarczyk
(74) *Attorney, Agent, or Firm* — Vincent Duffy

(57) ABSTRACT

Methods and systems for anomaly detection include encoding a time series with a time series encoder and encoding an event sequence with an event sequence encoder. A latent code is generated from outputs of the time series encoder and the event sequence encoder. The time series is reconstructed from the latent code using a time series decoder. The event sequence is reconstructed from the latent code using an event sequence decoder. An anomaly score is determined based on a reconstruction loss of the reconstructed time series and a reconstruction loss of the reconstructed event sequence. An action is performed responsive to the anomaly score.

16 Claims, 9 Drawing Sheets

(56) References Cited

OTHER PUBLICATIONS

Wu et al., "Multimodal Generative Models for Scalable Weakly-Supervised Learning", 32nd Conference on Neural Information Processing Systems (NeurIPS 2018), Dec. 2018, pp. 1-11.
Kingma et al., "Improved Variational Inference with Inverse Autoregressive Flow", 30th Conference on Neural Information Processing Systems (NIPS 2016), Dec. 2016, pp. 1-9.
He et al., "Drain: An Online Log Parsing Approach with Fixed Depth Tree", In2017 IEEE international conference on web services (ICWS) Jun. 25, 2017, pp. 33-40.

* cited by examiner

METRIC AND LOG JOINT AUTOENCODER FOR ANOMALY DETECTION IN HEALTHCARE DECISION MAKING

RELATED APPLICATION INFORMATION

This application claims priority to U.S. Patent Application No. 63/450,986, filed on Mar. 9, 2023, and to U.S. Patent Application No. 63/533,418, filed on Aug. 18, 2023, each incorporated herein by reference in its entirety.

BACKGROUND

Technical Field

The present invention relates to automated anomaly detection and, more particularly, to anomaly detection that is based on distinct modes of information.

Description of the Related Art

Anomaly detection helps to manage complex systems. A cyber-physical system may include a variety of sensors, which may collect a wide variety of information about the system, its operation, and its environment. The collected data may be used to characterize the operational characteristics of the cyber-physical system, for example to determine when the cyber-physical system may be operating outside its expected normal parameters.

SUMMARY

A method for anomaly detection includes encoding a time series with a time series encoder and encoding an event sequence with an event sequence encoder. A latent code is generated from outputs of the time series encoder and the event sequence encoder. The time series is reconstructed from the latent code using a time series decoder. The event sequence is reconstructed from the latent code using an event sequence decoder. An anomaly score is determined based on a reconstruction loss of the reconstructed time series and a reconstruction loss of the reconstructed event sequence. An action is performed responsive to the anomaly score.

A system for anomaly detection includes a hardware processor and a memory that stores a computer program. When executed by the hardware processor, the computer program causes the hardware processor to encode a time series with a time series encoder, to encode an event sequence with an event sequence encoder, to generate a latent code from outputs of the time series encoder and the event sequence encoder, to reconstruct the time series from the latent code using a time series decoder, to reconstruct the event sequence from the latent code using an event sequence decoder, to determine an anomaly score based on a reconstruction loss of the reconstructed time series and a reconstruction loss of the reconstructed event sequence, and to perform an action responsive to the anomaly score.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

A cyber-physical system may include a large number of sensors that monitor the working status of the system. Some of the information from the system may be collected as metrics in the form of a multivariate time series, where measurements from the sensors are made regularly and can be tracked over time. Examples of metrics include performance and resource counters (e.g., processor usage, memory usage, and free disk space) and hardware conditions (e.g., temperature and power consumption). Other information from the system may be collected as logs in the form of free-form text data with timestamps. Examples of logs include system logs and hardware logs.

The metrics and logs generated by a given system may be correlated. Proper interpretation of the system's status may therefore include a joint analysis of both. In using both modes of information, false alerts may be avoided and the accuracy of anomaly detection may be increased.

For example, a period of relatively high processor usage is expected if a large application is launched, but this metric may be deemed unusual if no such activities are recorded. In another example, a sudden burst of router events may be considered normal if it correlates with an increased number of users shown in the network traffic metrics. If the traffic metrics are normal instead, then the event burst may suggest a hardware failure and may be flagged as an anomaly.

Thus, time series metrics can be highly volatile and sensitive to the operating context of the system. A machine learning model that makes use of both metric time series information and system event sequences can characterize their joint dynamic behaviors under normal operating conditions to detect any deviation therefrom. Transformers and an attention mechanism can effectively model the interaction of the two forms of temporal data, which improves the sensitivity and robustness of anomaly detection, allowing for the explicit identification of events or metrics that cause a detected anomaly.

Toward that end, a joint variational autoencoder (VAE) model may be used, where metric time series and log event sequences are jointly encoded into a latent code before being reconstructed using respective decoders. An anomaly score can be determined based on the outputs of the decoders, for example by comparison of the reconstructed information to the actual inputs. The outputs of the encoders may be combined by concatenation or by a product-of-expert approach.

Figure 1:
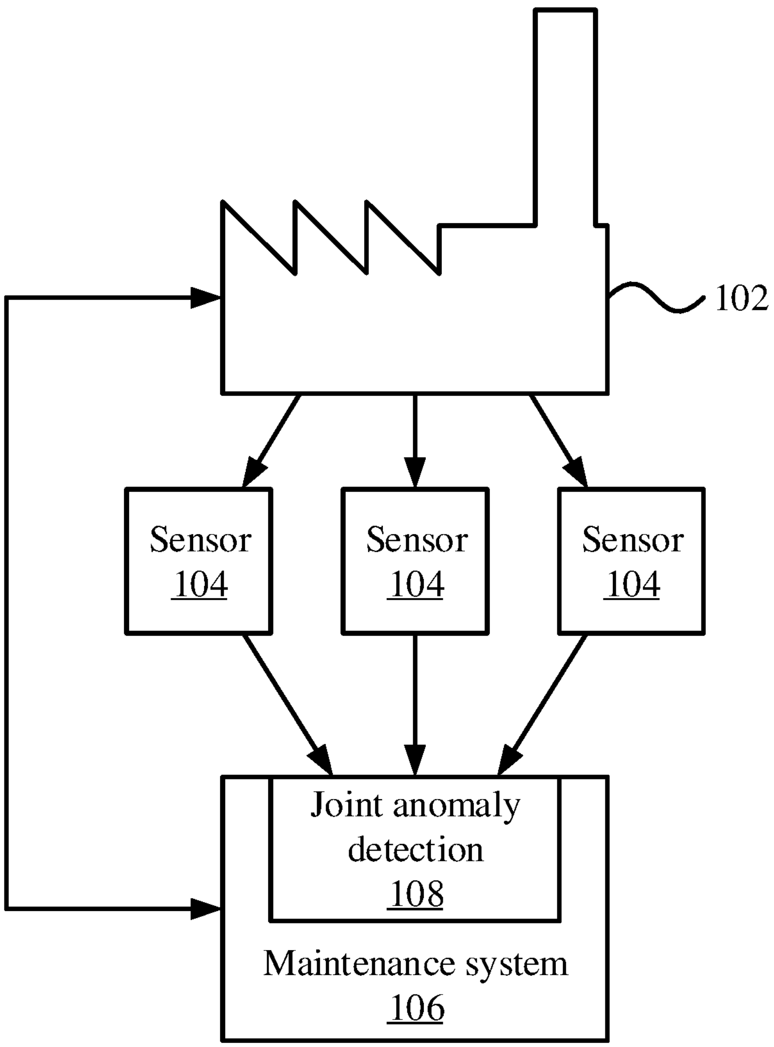
FIG. 1 is a diagram of a cyber-physical system with anomaly detection across metric time series and event sequence logs, in accordance with an embodiment of the present invention.

Referring now in detail to the figures in which like numerals represent the same or similar elements and initially to FIG. 1, a maintenance system 106 in the context of a monitored system 102 is shown. The monitored system 102 can be any appropriate system, including physical systems such as manufacturing lines and physical plant operations, electronic systems such as computers or other computerized devices, software systems such as operating systems and applications, and cyber-physical systems that combine physical systems with electronic systems and/or software systems. Exemplary systems 102 may include a wide range of different types, including railroad systems, power plants, vehicle sensors, data centers, satellites, and transportation systems. Another type of cyber-physical system can be a network of internet of things (IoT) devices, which may include a wide variety of different types of devices, with various respective functions and sensor types.

One or more sensors 104 record information about the state of the monitored system 102. The sensors 104 can be any appropriate type of sensor including, for example, physical sensors, such as temperature, humidity, vibration, pressure, voltage, current, magnetic field, electrical field, and light sensors, and software sensors, such as logging utilities installed on a computer system to record information regarding the state and behavior of the operating system and applications running on the computer system. The sensor data may include, e.g., numerical data and categorical or binary-valued data. The sensor data may be stored as log information that records the occurrence of discrete events. The information generated by the sensors 104 can be in any appropriate format and can include sensor log information generated with heterogeneous formats.

The sensors 104 may transmit the logged sensor information to an anomaly maintenance system 106 by any appropriate communications medium and protocol, including wireless and wired communications. The maintenance system 106 can, for example, identify abnormal or anomalous behavior by monitoring the multivariate time series and log information that are generated by the sensors 104. Once anomalous behavior has been detected, the maintenance system 106 communicates with a system control unit to alter one or more parameters of the monitored system 102 to correct the anomalous behavior.

Exemplary corrective actions include changing a security setting for an application or hardware component, changing an operational parameter of an application or hardware component (for example, an operating speed), halting and/or restarting an application, halting and/or rebooting a hardware component, changing an environmental condition, changing a network interface's status or settings, etc. The maintenance system 106 thereby automatically corrects or mitigates the anomalous behavior. By identifying the particular sensors 104 that are associated with the anomalous classification, the amount of time needed to isolate a problem can be decreased.

Each of the sensors 104 outputs a respective time series, which encodes measurements made by the sensor over time, or log of events. For example, the time series may include pairs of information, with each pair including a measurement and a timestamp, representing the time at which the measurement was made. Each time series may be divided into segments, which represent measurements made by the sensor over a particular time range. Time series segments may represent any appropriate interval, such as one second, one minute, one hour, or one day. Time series segments may represent a set number of collection time points, rather than a fixed period of time, for example covering 100 measurements. The logs may be segmented into similar periods of time.

The maintenance system 106 therefore includes a model that may be trained to handle time series data and log event categorical data. For a complicated system 106, the number of sensors 104 may be very large, with the sensors reporting independent streams of time-series data. The joint anomaly detection 108 therefore combines information from both types of sensor data with a joint VAE.

Sensors 104 may collect information about conditions of the system 106, such as information that relates to system control and operation mode. Sensors 104 may also collect information relating to key metrics such as temperature, humidity, motion, and pressure to characterize the system health. Monitoring for anomalies may be conducted on information from the time series sensors, but the values of the time series sensors are influenced by the system status as indicated by the logs.

In addition to cyber-physical systems 102, the system in question may relate to a patient in a healthcare setting. In such an example, the sensors 104 may monitor the patient's vital signs, while the event sequences may record discrete health events, such as seizures, treatment administrations, or other intermittent occurrences.

Figure 2:
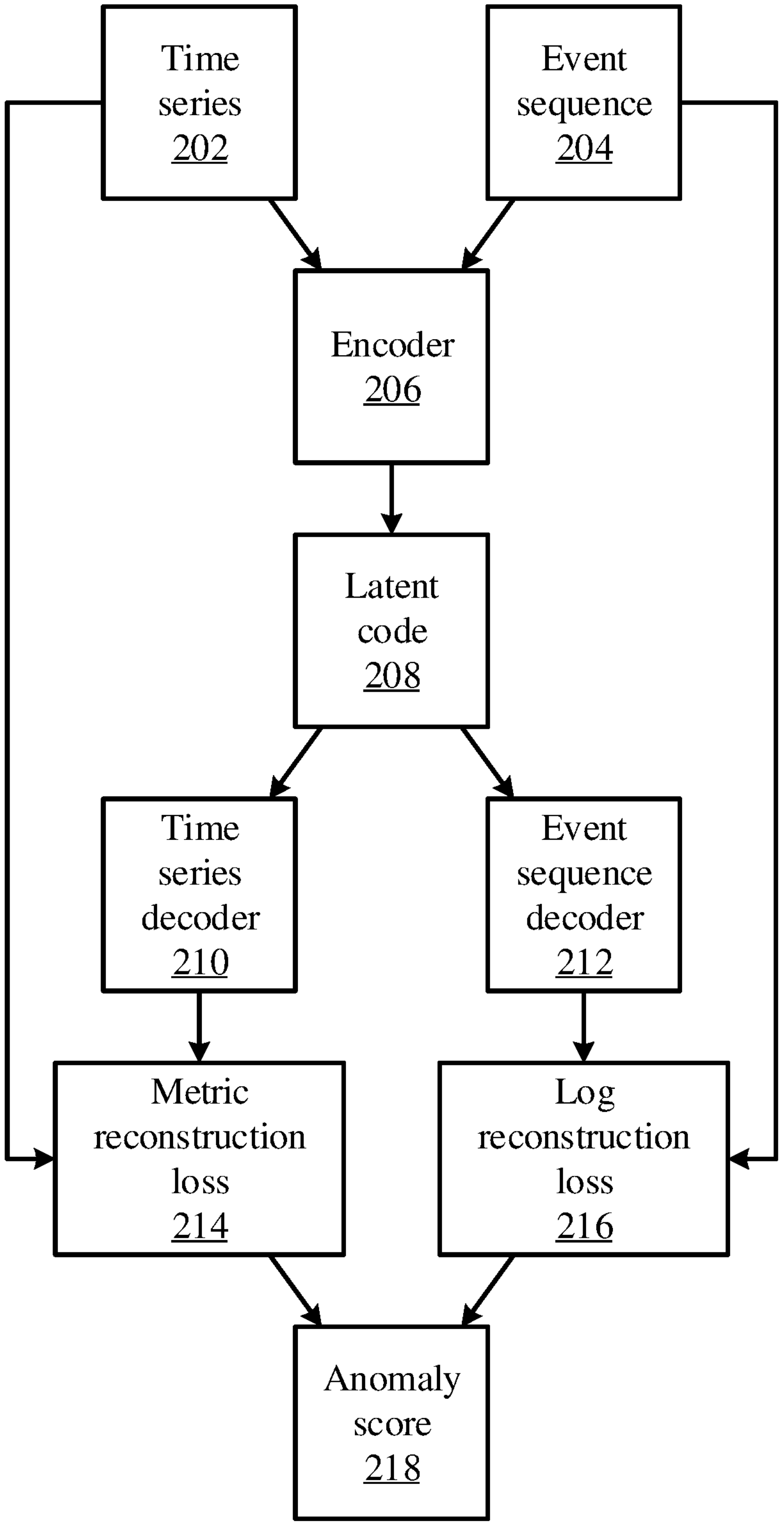
FIG. 2 is a block/flow diagram of a method/system for anomaly detection that makes use of a joint variational autoencoder, in accordance with an embodiment of the present invention.

Referring now to FIG. 2, a machine learning model for joint anomaly detection is shown. The model accepts as input a multivariate time series 202, reflecting measured metrics from a system 102, and an event sequence 204, representing event log information from the system 102. As noted above, the time series may include measurements from one or more sensors 104 over a predetermined time period, and the event sequence 204 may include time-stamped text entries that reflect events that occurred during the same time period. The two inputs may be synchronized and divided into rolling windows, with contemporaneous windows of each being considered as a joint input.

Both inputs are provided as joint input to encoder 206, which includes a time series encoder and an event sequence encoder. These encoders may be implemented as respective transformers, $E_{met}$ and $E_{log}$, with stacks of self-attention and cross-attention layers that fuse the information among different timestamps of each sequence. A shared time embedding layer may be learned using a time-to-vector conversion model to convert timestamps of the event sequence into a vector.

In the metric encoder, the time series are processed by a one-dimensional convolutional layer, with the result at each timestamp being concatenated with the corresponding time embedding vector, before being input to the transformer. In the event sequence encoder, the event sequences are first parsed by a log parser to decompose every event message into two parts: A template and parameters. For example, the message, "ESMCommonService has transitioned to the stopped state," may be converted to a template, "[*] has transitioned to the stopped state," with the parameter, "ESMCommonService." A template type embedding layer and a parameter embedding layer may be learned to convert the template type and parameters to vectors, respectively.

Hidden states of the encoders at a most recent timestep are denoted as $h_{met}$ and $h_{log}$:

$$h_{met} = E_{met}(x)$$

$$h_{log} = E_{log}(y)$$

The hidden states are combined to form a vector h that is used to compute vectors μ and Σ, which parameterize a posterior distribution q(z|x, y). These vectors are the mean and the covariance matrix of a Gaussian distribution, respectively:

$$q(z|x, y) = \mathcal{N}\left(z; \mu(x, y), \sum(x, y)\right)$$

The values for μ and Σ may be determined by concatenation or by product-of-experts. In a concatenation approach, $h=\text{concat}(h_{met}; h_{log})$, where $\mu=W_1h$ and $\Sigma=W_2h$. In a product-of-experts approach, $\mu_{met}=W_1h_{met}$, $\Sigma_{met}=W_2h_{met}$, $\mu_{log}=W_3h_{log}$, and $\Sigma_{log}=W_4h_{log}$, where μ, $\Sigma=\text{POE}(\Sigma_{met}, \Sigma_{met}, \mu_{log}, \Sigma_{log})$. The W values are learnable parameters.

A latent code z 208 is sampled from the distribution q(z|x, y) and represents the combined input in a latent space. That latent code 208 is subsequently decoded by a time series decoder 210 and an event sequence decoder 212, being used as the condition to the time series decoder p(x|z) and the event sequence decoder p(y|z).

The time series decoder 210 attempts to create an output that reconstructs the time series 202, and a metric reconstruction loss 214 identifies the difference between the two. The event sequence decoder 212 similarly attempts to create an output that reconstructs the event sequence 204, and a log reconstruction loss 216 identifies the difference between the two. The time series decoder 210 may be implemented as a transformer model that outputs a multivariate time series, while the event sequence decoder 212 may be implemented as a transformer model that outputs a sequence of log it vectors. The softmax of each log it vector gives the probability of the type of the event at that position.

The metric reconstruction error $\mathcal{L}_{met}$ may be defined as the mean-squared-error between the input metric time series x and the reconstructed time series $\hat{x}$:

$$\mathcal{L}_{met}(x, \hat{x}) = ||x - \hat{x}||_2^2$$

The log error $\mathcal{L}_{log}$ may be defined as the cross entropy between the reconstructed log its $\hat{Y}$ and the input events y:

$$\mathcal{L}_{log}\left(y, \hat{Y}\right) = \text{Cross Entropy}\left(y, \hat{Y}\right) = -\sum_{i=1}^{n} \log \hat{Y}_{y,i}$$

A regularization loss between the posterior distribution and a prior distribution p(z) can also be computed as:

$$\mathcal{L}_{reg}(x, y) = \max(b, D_{KL}(q(z|x, y), \mathcal{N}(0, 1)))$$

where b is a user-specified hyper-parameter that controls deviation of the posterior distribution q and the prior Gaussian distribution $\mathcal{N}(0,1)$ and where $D_{KL}$ is the Kullback-Leibler divergence.

An anomaly score 218 is determined for the time period of the time series 202 and the event sequence 204 based on the metric reconstruction loss 214 and the log reconstruction loss 216. The anomaly score may be computed as:

$$\text{Score}(x, y) = \mathcal{L}_{met}(x, G_{met}(\mu)) + \alpha\mathcal{L}_{log}(y, G_{log}(\mu))$$

where μ=μ(x, y). $G_{met}$ is the time series decoder 210 and $G_{log}$ is the event sequence decoder. The hyper-parameter a may be selected by a user using cross-validation to control the balance between the log reconstruction objective and the metrics reconstruction objective. A value τ represents the $99^{th}$ percentile of these scores and may be used as the detection threshold. If an anomaly score is greater than τ, then an anomaly has been detected.

The encoder 206, the time series decoder 210, and the event sequence decoder 212 may be trained on a set of training data that reflects normal operation of the system 102. The model is trained to optimize a weighted sum of the reconstruction errors. If the anomaly score is higher than a threshold, then an anomaly is detected and a ranked list of metrics and events that are potential causes of the anomaly is generated.

Figure 3:
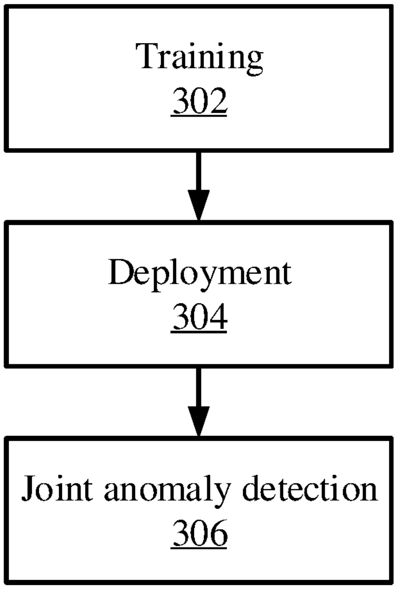
FIG. 3 is a block/flow diagram of a method for anomaly detection that includes training and deploying a joint variational autoencoder, in accordance with an embodiment of the present invention.

Referring now to FIG. 3, a method for training and using a joint VAE model for anomaly detection is shown. Block 302 trains the model using training data that represents normal operation of the system 102. This training data includes both event sequence data and time series data collected from the system 102 at the same time. The trained model is then deployed 304 to be implemented in the maintenance system 106. As new data is collected from sensors 104, the trained model is used to identify anomalies in the operation of the system 102.

Figure 4:
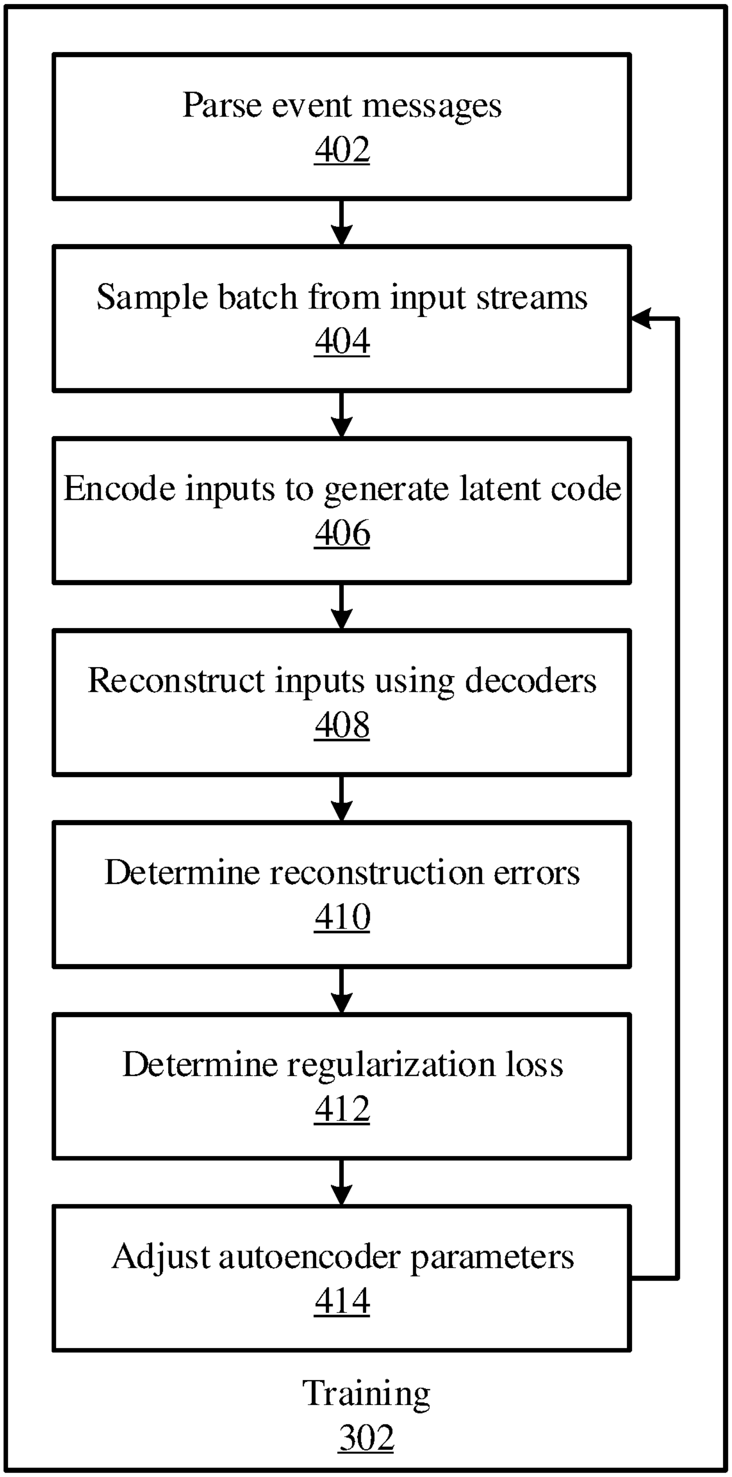
FIG. 4 is a block/flow diagram of a method for training a joint variational autoencoder for anomaly detection, in accordance with an embodiment of the present invention.

Referring now to FIG. 4, additional detail on the training 302 of the anomaly detection model is shown. Given a training dataset of synchronized metric time series and event logs, the respective inputs can be split into segments using overlapping rolling windows of fixed time length. Block 402 samples event messages from the event sequence input, identifying event types from each log message as an integer value. For each event in the sequence, a template type embedding vector, a parameter embedding vector, and a time embedding vector may be concatenated for use as input to the encoder.

Block 404 samples batches from the input streams, for example identifying a time window and taking the events and time series measurements that occur within that time window. The encoder 206 encodes the different inputs in block 406 to generate respective latent codes, which may be combined together. Block 408 then uses the time series decoder 210 and the event sequence decoder 212 to reconstruct the respective inputs.

Block 410 determines the reconstruction errors $\mathcal{L}_{met}$ and $\mathcal{L}_{log}$ and block 412 determines the regularization loss $\mathcal{L}_{reg}$ as described above. Block 414 adjusts autoencoder parameters according to these losses. A total loss may be calculated in block 414 as a weighted average of two reconstruction errors and the regularization loss:

$$\mathcal{L}=\mathbb{E}_{x,y\in D}\left[\mathbb{E}_{z\sim q(\cdot x,y)}[\mathcal{L}_{met}(x,G_{met}(z))+\alpha\mathcal{L}_{log}(y,G_{log}(z))]+\beta\mathcal{L}_{reg}(x,y)\right]$$

where α and β are weighting hyperparameters and D is the training dataset of pairs, where the metric input x and corresponding log input y are sampled from D. The loss may be minimized by block 414 using, e.g., a stochastic gradient descent. Based on the loss, block 414 adjusts parameters of the neural networks making up the encoder 206 and the decoders 210/212.

This process may be repeated until a termination condition is reached. For example, termination conditions may include exhaustion of available training data, a predetermined number of iterations, or convergence of the parameters (e.g., a magnitude of successive changes falling below a threshold). Scores may be determined for each window of the training data.

Figure 5:
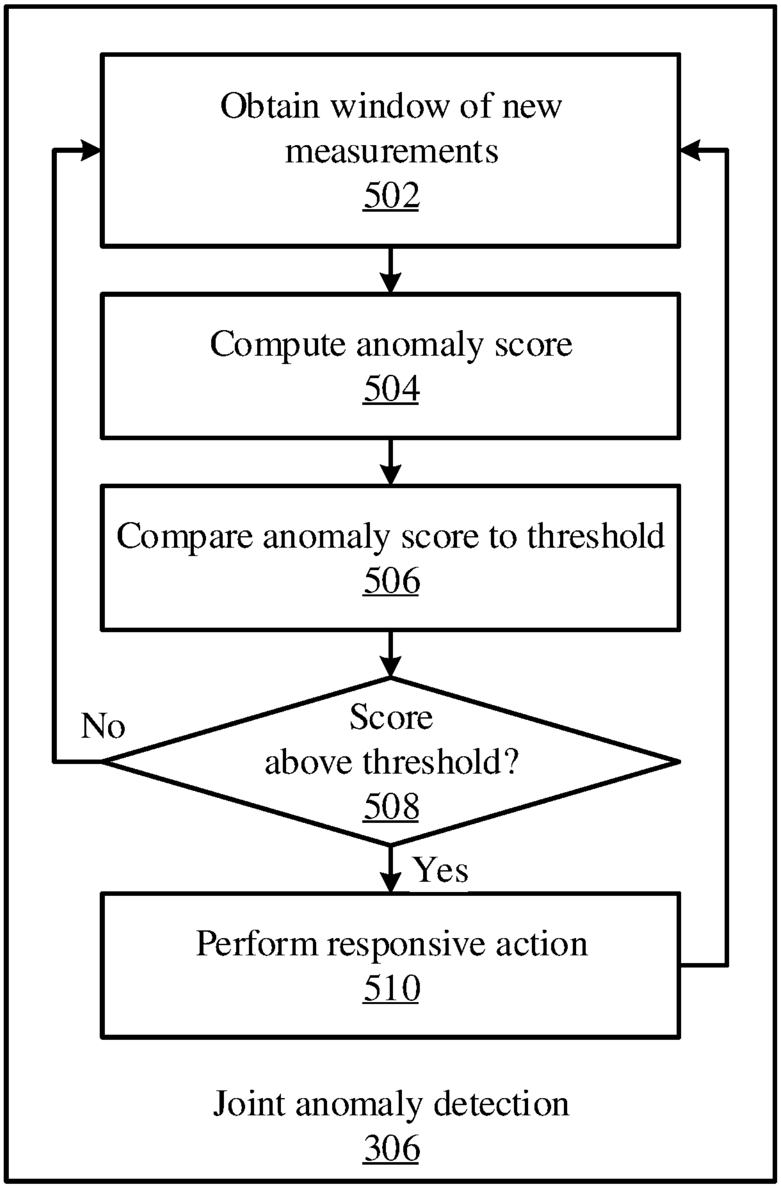
FIG. 5 is a block/flow diagram of a method for joint anomaly detection using metric time series and event sequence logs, in accordance with an embodiment of the present invention.

Referring now to FIG. 5, additional detail on joint anomaly detection 306 is shown. Block 502 obtains new measurements from the sensors 104 and logs, for example collecting all such measurements and events that occur within a given window of time. Block 504 uses the trained encoder 206 and decoders 210/212 to generate an anomaly score 218 for the new measurements, for example using the model of FIG. 2.

Block 506 compares the anomaly score to the threshold value t, or any other appropriate threshold value. If block 508 determines that the anomaly score falls below the threshold, then processing returns to block 502 to obtain a new set of measurements. If the anomaly score is above the threshold, then block 510 triggers the performance of an action responsive to the detected anomaly, at which point processing returns to block 502 again.

The responsive action may act to correct or mitigate the effect of the anomaly. For example, in a system 102 that represents a factory, the response may be to shut down production to prevent damage or hazardous conditions. In a system 102 that represents a computer system, the action may be to shut down processes or otherwise decrease the computational load to prevent overheating.

In a system 102 that is implemented in a healthcare setting, the sensors 104 may relate to monitors of a patient's health. The responsive action may therefore relate to an automated adjustment of the patient's treatment. For example, if an anomaly is detected during the administration of a treatment, the responsive action may be to halt the treatment or otherwise intervene.

The anomaly detection may include the identification of a ranked list of metrics and events that are potential causes of a detected anomaly. To rank the metrics, the reconstruction error of each metric may be averaged over time, with the metrics being ranked in descending order of this averaged error. For event sequences, the probability of each ground-truth event may be calculated according to the predicted log its, and the events may be ranked from low probability to high probability. In both lists, candidates near the top of the list are more likely to be the cause of the anomaly. The responsive action may therefore focus on actions that relate to high-ranked metrics and events. For example, if an anomaly is detected and the system's temperature is ranked highly, then the automated response may be to adjust environmental conditions or to adjust computational load.

Figure 6:
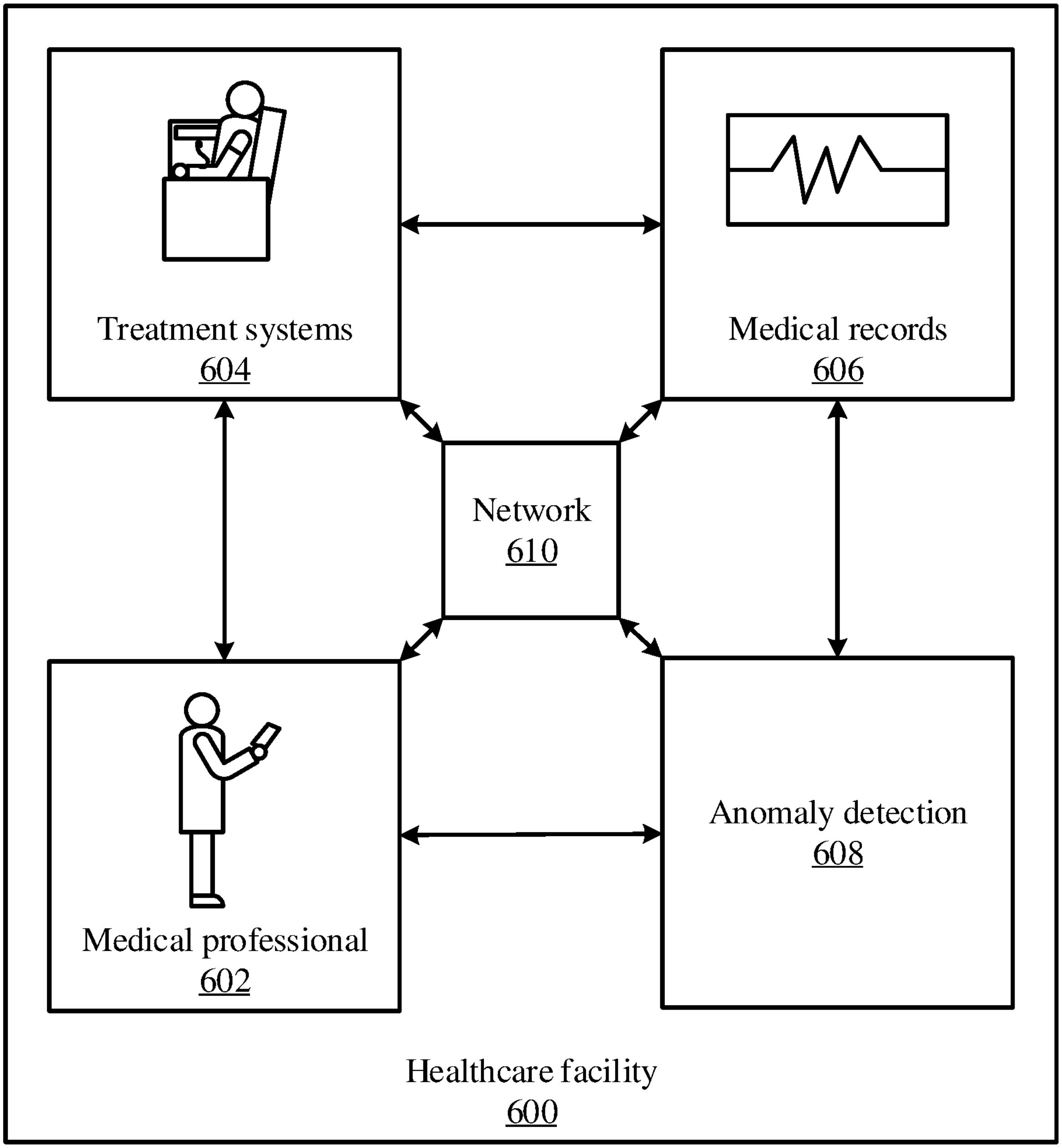
FIG. 6 is a block diagram of a healthcare facility where joint anomaly detection is used to guide medial professionals and patient treatments, in accordance with an embodiment of the present invention.

Referring now to FIG. 6, a diagram of anomaly detection is shown in the context of a healthcare facility 600. Anomaly detection may be used to determine when a patient's healthcare needs have changed, for example in response to an adverse health event or a negative reaction to a treatment. A change in treatment may be automatically triggered or administered to aid the patient.

The healthcare facility may include one or more medical professionals 602 who provide information relating to events and measurements of system status to anomaly detection 608. Treatment systems 604 may furthermore monitor patient status to generate medical records 606 and may be designed to automatically administer and adjust treatments as needed. In some cases, the medical records 606 may include multivariate time series relating to the patient's condition (e.g., heart rate, blood oxygen levels, blood pressure, etc.). The medical records 606 may further include event sequences relating to healthcare events, such as administration of a treatment or a healthcare event that occurs intermittently.

Based on information drawn from at least the medical professionals 602, treatment systems 604, and medical records 606, anomaly detection 608 identifies an anomalous health condition for the patient and identifies metrics and/or events that contribute to that anomaly. Information about the detected anomaly may be forwarded to medical professionals 602 to diagnose and treat patient conditions.

The different elements of the healthcare facility 600 may communicate with one another via a network 610, for example using any appropriate wired or wireless communications protocol and medium. Thus the anomaly detection 608 may access remotely stored medical records 606, may communicate with the treatment systems 604, and may receive instructions and send reports to medical professionals 602. In particular, the anomaly detection 608 may automatically trigger treatment changes for a patient, responsive to new information gleaned from the medical records 606, by sending instructions to the treatment systems 604. For example, the treatment systems may automatically administer a drug or shut down treatment responsive to a negative health event.

In some cases, the anomaly detection 608 may trigger a treatment for the patient responsive to a particular event or metric being ranked as likely to have contributed to the anomaly. For example, if the anomaly is associated with a measurement of the patient's blood pressure, the treatment systems 604 may adjust dosage of automatically administered blood pressure medication. The output of the anomaly detection 608 may therefore include one or a combination of the above automatic treatments and notifying medical professionals 602. In some cases, the treatment plan may be used by a medical professional to assist in decision-making for patient management. For example, upon being informed of a change in a patient's condition, the healthcare professional 602 may go to the patient to check on them.

Figure 7:
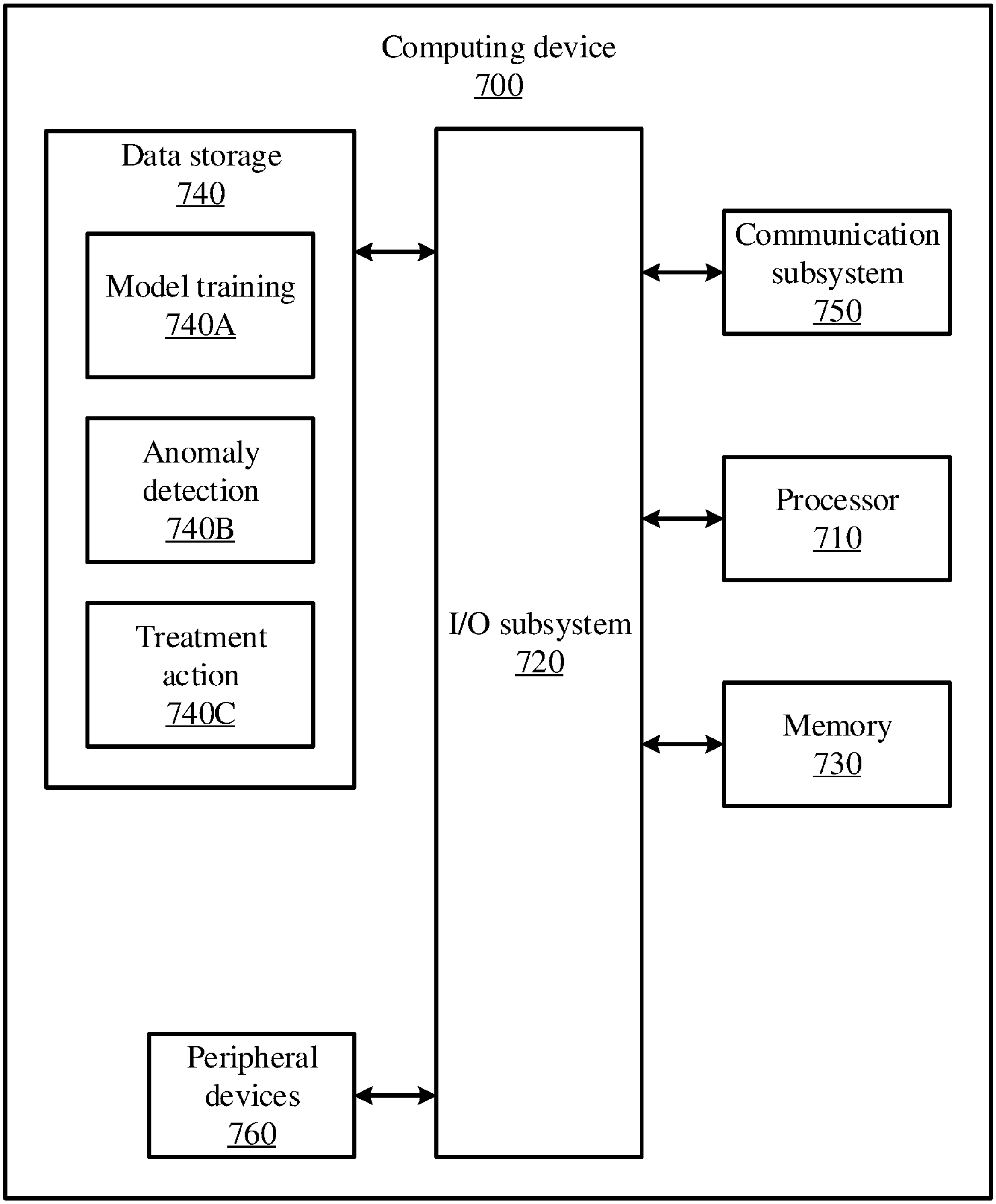
FIG. 7 is a block diagram of a computer device for performing anomaly detection, in accordance with an embodiment of the present invention.

Referring now to FIG. 7, an exemplary computing device 700 is shown, in accordance with an embodiment of the present invention. The computing device 700 is configured to perform anomaly detection.

The computing device 700 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 700 may be embodied as one or more compute sleds, memory sleds, or other racks, sleds, computing chassis, or other components of a physically disaggregated computing device.

As shown in FIG. 7, the computing device 700 illustratively includes the processor 710, an input/output subsystem 720, a memory 730, a data storage device 740, and a communication subsystem 750, and/or other components and devices commonly found in a server or similar computing device. The computing device 700 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 730, or portions thereof, may be incorporated in the processor 710 in some embodiments.

The processor 710 may be embodied as any type of processor capable of performing the functions described herein. The processor 710 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 730 may be embodied as any type of volatile or non-volatile memory or data storage capable of performing the functions described herein. In operation, the memory 730 may store various data and software used during operation of the computing device 700, such as operating systems, applications, programs, libraries, and drivers. The memory 730 is communicatively coupled to the processor 710 via the I/O subsystem 720, which may be embodied as circuitry and/or components to facilitate input/output operations with the processor 710, the memory 730, and other components of the computing device 700. For example, the I/O subsystem 720 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 720 may form a portion of a system-on-a-chip (SOC) and be incorporated, along with the processor 710, the memory 730, and other components of the computing device 700, on a single integrated circuit chip.

The data storage device 740 may be embodied as any type of device or devices configured for short-term or long-term storage of data such as, for example, memory devices and circuits, memory cards, hard disk drives, solid state drives, or other data storage devices. The data storage device 740 can store program code 740A for model training, 740B for anomaly detection, and/or 740C for performing a corrective action responsive to a detected anomaly. Any or all of these program code blocks may be included in a given computing system. The communication subsystem 750 of the computing device 700 may be embodied as any network interface controller or other communication circuit, device, or collection thereof, capable of enabling communications between the computing device 700 and other remote devices over a network. The communication subsystem 750 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 700 may also include one or more peripheral devices 760. The peripheral devices 760 may include any number of additional input/output devices, interface devices, and/or other peripheral devices. For example, in some embodiments, the peripheral devices 760 may include a display, touch screen, graphics circuitry, keyboard, mouse, speaker system, microphone, network interface, and/or other input/output devices, interface devices, and/or peripheral devices.

Of course, the computing device 700 may also include other elements (not shown), as readily contemplated by one of skill in the art, as well as omit certain elements. For example, various other sensors, input devices, and/or output devices can be included in computing device 700, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 700 are readily contemplated by one of ordinary skill in the art given the teachings of the present invention provided herein.

Figure 8:
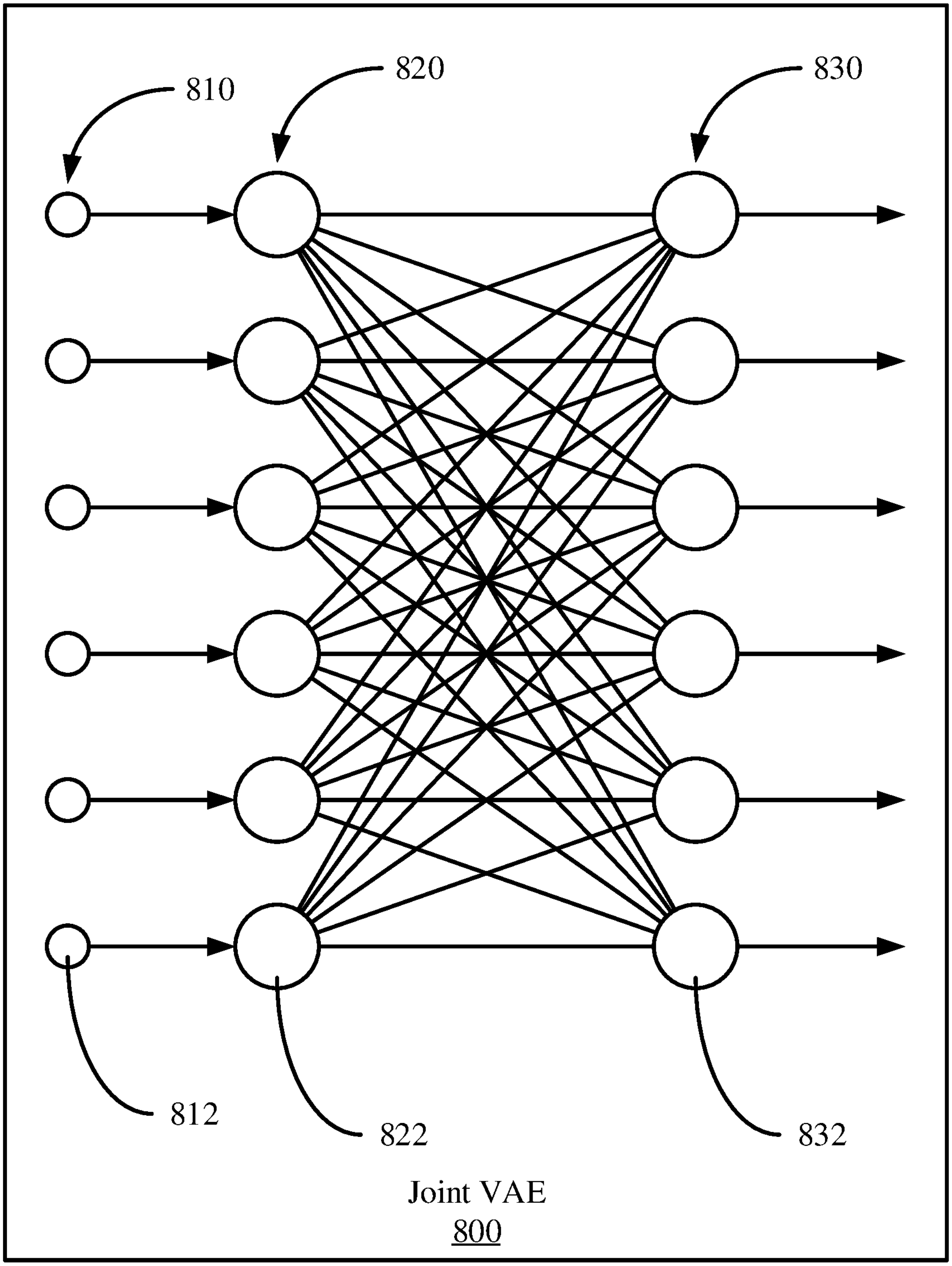
FIG. 8 is a diagram of an exemplary neural network architecture that may be used as part of a variational autoencoder, in accordance with an embodiment of the present invention.
Figure 9:
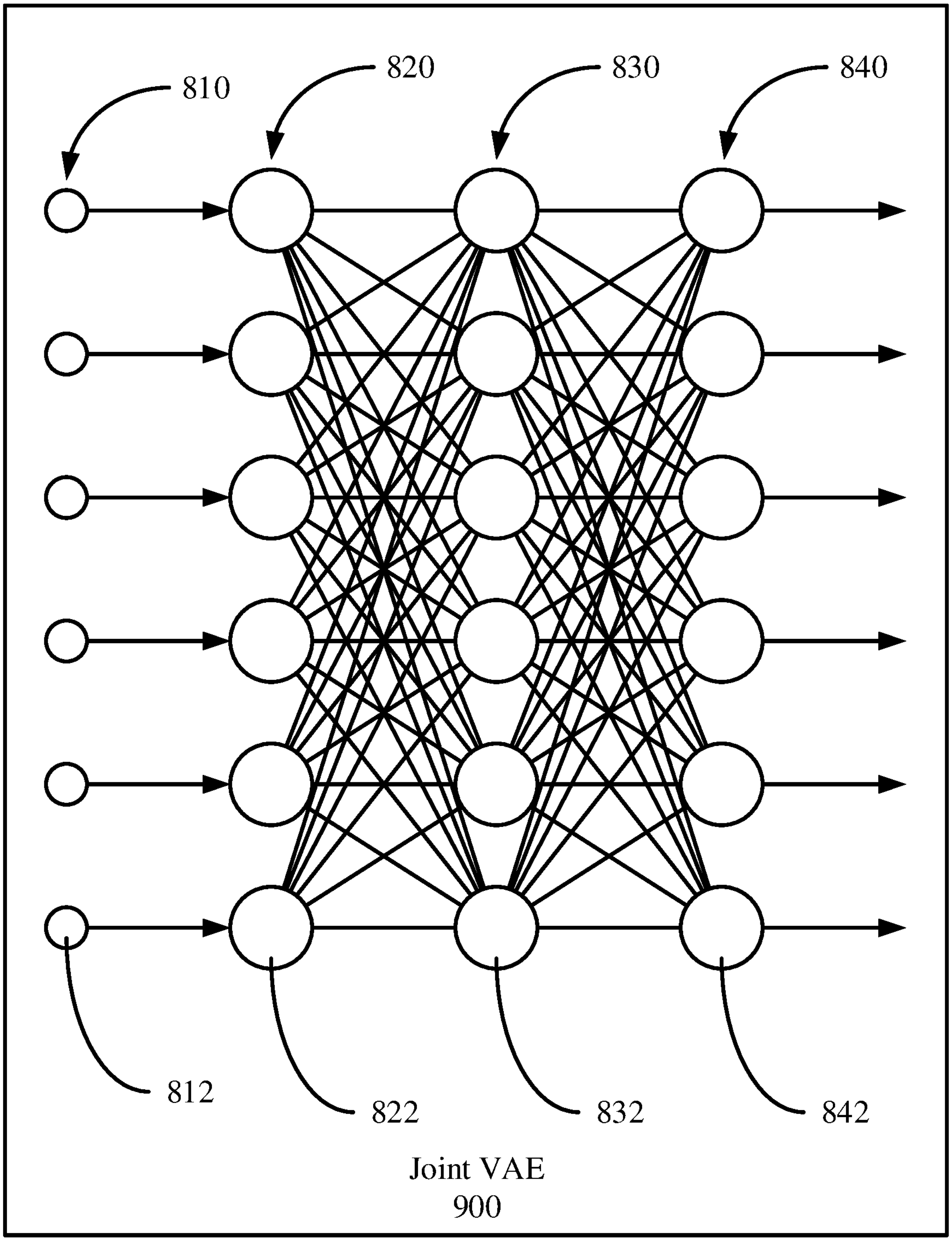
FIG. 9 is a diagram of an exemplary deep neural network architecture that may be used as part of a variational autoencoder, in accordance with an embodiment of the present invention.

Referring now to FIGS. 8 and 9, exemplary neural network architectures are shown, which may be used to implement parts of the present models, such as joint VAEs 800 and 900. A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the input data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

In layered neural networks, nodes are arranged in the form of layers. An exemplary simple neural network has an input layer 820 of source nodes 822, and a single computation layer 830 having one or more computation nodes 832 that also act as output nodes, where there is a single computation node 832 for each possible category into which the input example could be classified. An input layer 820 can have a number of source nodes 822 equal to the number of data values 812 in the input data 810. The data values 812 in the input data 810 can be represented as a column vector. Each computation node 832 in the computation layer 830 generates a linear combination of weighted values from the input data 810 fed into input nodes 820, and applies a non-linear activation function that is differentiable to the sum. The exemplary simple neural network can perform classification on linearly separable examples (e.g., patterns).

A deep neural network, such as a multilayer perceptron, can have an input layer 820 of source nodes 822, one or more computation layer(s) 830 having one or more computation nodes 832, and an output layer 840, where there is a single output node 842 for each possible category into which the input example could be classified. An input layer 820 can have a number of source nodes 822 equal to the number of data values 812 in the input data 810. The computation nodes 832 in the computation layer(s) 830 can also be referred to as hidden layers, because they are between the source nodes 822 and output node(s) 842 and are not directly observed. Each node 832, 842 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the input data. A deep neural network can be fully connected, where each node in a computational layer is connected to all other nodes in the previous layer, or may have other configurations of connections between layers. If links between nodes are missing, the network is referred to as partially connected.

Training a deep neural network can involve two phases, a forward phase where the weights of each node are fixed and the input propagates through the network, and a backwards phase where an error value is propagated backwards through the network and weight values are updated.

The computation nodes 832 in the one or more computation (hidden) layer(s) 830 perform a nonlinear transformation on the input data 812 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for anomaly detection, comprising:

encoding a time series with a time series encoder of a joint variational autoencoder trained to detect anomalies from both time series and event sequences;

encoding an event sequence with an event sequence encoder of the joint variational autoencoder;

generating a latent code from outputs of the time series encoder and the event sequence encoder by fusing information from different timestamps of sequences within hidden states of the time series encoder and the event sequence encoder;

reconstructing the time series from the latent code using a time series decoder of the joint variational autoencoder; and reconstructing the event sequence from the latent code using an event sequence decoder of the joint variational autoencoder;

determining, with the joint variational autoencoder, an anomaly score based on a reconstruction loss of the reconstructed time series and a reconstruction loss of the reconstructed event sequence; and performing a corrective action with the joint variational autoencoder by altering parameters of a monitored system that mitigates anomalous behavior of the monitored system responsive to the anomaly score that exceeded a threshold that identified the anomalous behavior in a patient health condition in a healthcare setting, the corrective action including a treatment action responsive to the patient health condition to automatically administer an adjusted dosage of a blood pressure treatment to the patient having blood pressure issues.

2. The method of claim 1, further comprising determining a ranked list of metrics and a ranked list of events.

3. The method of claim 2, wherein determining the ranked list of metrics includes averaging the reconstruction loss of the reconstructed time series for each of a plurality of metrics represented in the time series and ranking the metrics in descending order.

4. The method of claim 2, wherein determining the ranked list of events includes calculating a probability of ground-truth events according to predicted log its and ranking the events from low probability to high probability.

5. The method of claim 2, wherein the action is directed to one or more highly ranked metrics or events.

6. The method of claim 1, wherein determining the anomaly score includes a weighted sum of the reconstruction loss of the reconstructed time series and the reconstruction loss of the reconstructed event sequence.

7. The method of claim 1, wherein the time series encoder, the event sequence encoder, the time series decoder, and the event sequence decoder make up a joint variational autoencoder that includes a machine learning model trained to reconstruct inputs after conversion Into a latent space.

8. The method of claim 1, wherein generating the latent code includes combining the outputs as a product of expert.

9. A system for anomaly detection, comprising:

a hardware processor; and a memory that stores a computer program which, when executed by the hardware processor, causes the hardware processor to:

encode a time series with a time series encoder of a joint variational autoencoder trained to detect anomalies from both time series and event sequences;

encode an event sequence with an event sequence encoder of the joint variational autoencoder, generate a latent code from outputs of the time series encoder and the event sequence encoder by fusing information from different timestamps of sequences within hidden states of the time series encoder and the event sequence encoder;

reconstruct the time series from the latent code using a time series decoder of the joint variational autoencoder; and reconstruct the event sequence from the latent code using an event sequence decoder of the joint variational autoencoder;

determine, with the joint variational autoencoder, an anomaly score based on a reconstruction loss of the reconstructed time series and a reconstruction loss of the reconstructed event sequence; and perform a corrective action with the joint variational autoencoder by altering parameters of a monitored system that mitigates anomalous behavior of the monitored system responsive to the anomaly score that exceeded a threshold that identified the anomalous behavior in a patient health condition in a healthcare setting, the corrective action including a treatment action responsive to the patient health condition to automatically administer an adjusted dosage of a blood pressure treatment to the patient having blood pressure issues.

10. The system of claim 9, wherein the computer program further causes the hardware processor to determine a ranked list of metrics and a ranked list of events.

11. The system of claim 10, wherein the computer program further causes the hardware processor to average the reconstruction loss of the reconstructed time series for each of a plurality of metrics represented in the time series and ranking the metrics in descending order.

12. The system of claim 10, wherein the computer program further causes the hardware processor to calculate a probability of ground truth events according to predicted log its and ranking the events from low probability to high probability.

13. The system of claim 10, wherein the action is directed to one or more highly ranked metrics or events.

14. The system of claim 9, wherein the computer program further causes the hardware processor to determine weighted sum of the reconstruction loss of the reconstructed time series and the reconstruction loss of the reconstructed event sequence.

15. The system of claim 9, wherein the time series encoder, the event sequence encoder, the time series decoder, and the event sequence decoder make up a joint variational autoencoder that includes a machine learning model trained to reconstruct inputs after conversion into a latent space.

16. The system of claim 9, wherein the computer program further causes the hardware processor to combine the outputs as a product of expert for the latent code.

* * * * *